(12) United States Patent
Tarrand

(10) Patent No.: US 8,512,724 B2
(45) Date of Patent: Aug. 20, 2013

(54) ANTISEPTIC COMPOSITIONS

(75) Inventor: Jeffrey J. Tarrand, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1275 days.

(21) Appl. No.: 11/916,972

(22) PCT Filed: Jun. 9, 2006

(86) PCT No.: PCT/US2006/022752
§ 371 (c)(1),
(2), (4) Date: Sep. 3, 2008

(87) PCT Pub. No.: WO2006/135854
PCT Pub. Date: Dec. 21, 2006

(65) Prior Publication Data
US 2009/0162301 A1 Jun. 25, 2009

Related U.S. Application Data

(60) Provisional application No. 60/689,634, filed on Jun. 10, 2005.

(51) Int. Cl.
*C11D 3/48* (2006.01)

(52) U.S. Cl.
USPC ........... 424/405; 424/401; 424/404; 510/108; 510/391

(58) Field of Classification Search
None
See application file for complete search history.

(56) References Cited

U.S. PATENT DOCUMENTS

| | | | |
|---|---|---|---|
| 3,671,654 A | 6/1972 | Nosler et al. | 424/312 |
| 3,743,727 A | 7/1973 | Herschler | 424/181 |
| 4,374,126 A * | 2/1983 | Cardarelli et al. | 514/772.6 |
| 4,469,702 A | 9/1984 | Schulte | 424/308 |
| 4,497,824 A | 2/1985 | Schulte | 514/166 |
| 4,507,287 A | 3/1985 | Dixon | 514/43 |
| 4,525,354 A | 6/1985 | Birch et al. | 424/115 |
| 4,626,530 A | 12/1986 | Schulte | 514/166 |
| 4,725,271 A | 2/1988 | Korol | 604/368 |
| 5,357,636 A | 10/1994 | Dresdner et al. | 2/161.7 |
| 5,753,270 A | 5/1998 | Beauchamp et al. | 424/667 |
| 5,962,538 A * | 10/1999 | Wiltzer et al. | 521/48 |
| 6,160,033 A | 12/2000 | Nies | 523/116 |
| 6,183,766 B1 | 2/2001 | Sine et al. | 424/405 |
| 6,875,422 B2 * | 4/2005 | Nonomura et al. | 424/49 |
| 6,986,897 B1 * | 1/2006 | Roberts et al. | 424/402 |
| 2003/0147925 A1* | 8/2003 | Sawan et al. | 424/400 |

OTHER PUBLICATIONS

Barenfanger et al., "Comparison of chlorhexidine and tincture of iodine for skin antisepsis in preparation for blood sample collection," *Journal Clin. Microbiol.*, 42:2216-7, 2004.
Chan, "Antimicrobial effect of resveratrol on dermatophytes and bacterial pathogens of the skin," *Biochemical Pharmacology*, 63:99-104, 2002.
Dewar and Gravens, "Effectiveness of septisol antiseptic foam as a surgical scrub agent," *Applied Microbiology*, 26:544-49, 1973.
Mannan et al., "Mistaken identity of skin cleaning solution leading to extensive chemical burns in an extremely preterm infant," *Acta Paediatrica.*, 96:1536-7, 2007.
McCoy et al., "Adverse events associated with chlorhexidine use: results from the Department of Veterans Affairs Dental Diabetes Study," *Journal of the American Dental Association*, 139:178-83, 2008.
Mimoz et al., "Chlorhexidine-based antiseptic solution vs alcohol-based povidone-iodine for central venous catheter care," *Archives of Internal Medicine*, 167:2066-72, 2007.
Pineda et al., "Azoospermia in dogs induced by injection of sclerosing agents to the caudae of the epididymides," *American Journal of Veterinary Research*, 38:831-8, 1977.
Prüss-Üstün et al., "Sharp injuries: global burden of disease from sharp injuries to health-care workers," Environmental Burden of Disease Series, No. 3, World Health Organization Protection of the Human Environment, Geneva 2003.
Seal and Paul-Cheadle, "A systems approach to preoperative surgical patient skin preparation," *Am. J. Infect. Control.*, 32:57-62, 2004.
Search Report and Written Opinion, issued in International Application No. PCT/US06/22752, dated Nov. 22, 2006.
Smith et al., "Microbial synergy via an ethanol-triggered pathway," *Mol. Cell. Bio.*, 24:3874-3884, 2004.
Tarrand and Gröschel, "Rapid, modified oxidase test for oxidase-variable bacterial isolates," *J. Clin. Microbiol.*, 16:772-774, 1982.
Trautner et al., "Skin antisepsis kits containing alcohol and chlorhexidine gluconate or tincture of iodine are associated with low rates of blood culture contaminations," *Infect. Control Hosp. Epidemiol.*, 23:397-401, 2002.
Van Luuren et al., "Anaphylactic reactions to chlorhexidine during urinary catheterization," *Nederlands Tijdschrift voor Geneeskunde*, 151:2531-4, 2007.
Widmer and Frei, "Decontamination, disinfection, and sterilization," In: P.R. Murray, E.J. Baron, M.A. Pfaller, J.H. Jorgensen, and R.H. Yolken (ed.), Manual of clinical microbiology, $9^{th}$ ed. ASM Press, Washington, DC, 2007.

* cited by examiner

*Primary Examiner* — Lakshmi Channavajjala
(74) *Attorney, Agent, or Firm* — Parker Highlander PLLC

(57) ABSTRACT

The present invention provides antiseptic compositions that contain DMSO or DMA, an alcohol (e.g., isopropanol), and/or an additional antiseptic agent such as iodine. In certain embodiments, the antiseptic compositions may be used for skin disinfection and/or skin antisepsis (e.g., as applied via a swab).

22 Claims, No Drawings

ANTISEPTIC COMPOSITIONS

This application is a national phase application under 35 U.S.C. §371 of International Application No. PCT/US2006/022752 filed Jun. 9, 2006, which claims the benefit of U.S. Provisional Application Ser. No. 60/689,634 filed Jun. 10, 2005, the entire contents and disclosures of which are specifically incorporated by reference herein without disclaimer.

BACKGROUND OF THE INVENTION

1. Field of the Invention

The present invention relates generally to the fields of microbiology, medicine and hygiene. More particularly, it concerns antiseptic compositions that may be used, in certain embodiments, for skin disinfection and/or skin antisepsis.

2. Description of Related Art

Antiseptics are crucial for the practice of medicine; however, currently used antiseptics have a significant failure rate which results in substantial additional medical costs. Antiseptics are commonly used prior to routine phlebotomy, in preparation for minor and major invasive procedures, and as part of routine infection control hand-washing practices. The failure of antiseptics often result in nosocomial infections and erroneous diagnostic tests. For example, it has been estimated that a single false positive blood culture (i.e., where the culture indicates that the blood has been infected with bacteria, although the blood was contaminated during the blood draw) done on blood drawn from a patient at a hospital costs the patient an additional $2000 to $4,200 in unnecessary medication, additional follow up testing, and increased length of stay. (Bates, 1991).

Attempts have been made to improve antiseptics. For example, skin antisepsis has been performed using 70% isopropyl alcohol containing either 2% chlorhexidine gluconate or 2% tincture of iodine (Trautner et al., 2002). Bacterial decontamination of skin, however, is difficult to achieve. For example, bacteria can colonize sweat glands, hair follicles, and become sequestered in layers of dead keratinized skin. Thus, there remains a significant need for improved antiseptics.

An improved antiseptic could lower rates of wound infection, catheter infection, and blood culture contamination, as well as reduce nosocomial contamination introduced from health care worker hands. Although rare, routine phlebotomy carries some finite risk of cellulitis. Thus, an improved antiseptic may become the standard even in standard procedures such as routine phlebotomy.

Higher concentrations of DMSO have been previously used for delivery of therapeutic compositions. U.S. Pat. No. 3,671,654 describes compositions comprising a diester of 2,2,4-trimethylpentanediol-1,3, an aliphatic carboxylic acid of 2 to 12 carbon atoms, a lower concentration of alcohol (e.g., 5% to 30%) and DMSO (e.g., 50% DMSO) for the treatment fungal or bacterial infections. DMSO, at concentrations of 50% or greater, is a common carrier used to get deep penetration of topical pharmaceuticals into the dermis and facilitate the absorption of drugs (Wilson et al., 1965). DMSO, has also been associated with anti-inflammatory effects.

Specifically, there is a clinical need for improved skin antiseptics. Current skin antiseptics have a significant failure rate, with adverse impact on surgical wound infection rates and infection control generally. Between 3 and 7% of blood cultures obtained in the U.S. become contaminated with skin flora at the time of phlebotomy with an associated cost of approximately $1 billion. Clean surgical wound contamination is a major problem and is largely due to the failure of skin antisepsis. In spite of this there have been only minor improvements in the performance of skin antiseptics in recent years. (whqlibdoc.who.int/publications/2003/9241562463.pdf; www.ahrq.gov/data/hcup/hcupnet.htm; CDC Advance Vol 329: Jun. 19, 2002; Boyce, 2001)

SUMMARY OF THE INVENTION

The present invention overcomes limitations in the prior art by providing an improved antiseptic. The inventor has made the surprising discovery that the inclusion of a low concentration of a dipolar aprotic solvent (e.g., DMSO or DMA at a concentration of less than about 30%) in an antiseptic (e.g., an antiseptic comprising an alcohol and/or an iodophor) results in a dramatic improvement in the antimicrobial properties of the antiseptic.

An aspect of the present invention relates to an antiseptic comprising a dipolar aprotic solvent and at least one of the following: (a) an alcohol, wherein the alcohol comprises at least about 40% of the antiseptic; or (b) atomic iodine or an iodophor; wherein the dipolar aprotic solvent comprises less than about 30% of the antiseptic; and wherein if the dipolar aprotic solvent is acetone, then the acetone comprises between from about 3% to about 30% of the antiseptic. In certain embodiments, the antiseptic comprises the polar aprotic solvent, the alcohol, and not atomic iodine or an iodophor. In other embodiments, the antiseptic comprises the polar aprotic solvent, atomic iodine or an iodophor, and not the alcohol. In certain embodiments, the antiseptic comprises the polar aprotic solvent plus both atomic iodine or an iodophor, and the alcohol. The antiseptic may comprise less than about 10% free iodine or less than about 2% free iodine.

In certain embodiments, the polar aprotic solvent is DMSO, DMA, tetrahydrofuran, methyl ethyl ketone, ethyl acetate, acetonitrile, n,n-dimethylformamide (DMF), acetone, DMAC, NMP, or pyridine. The antiseptic may be comprised in a "Sepp" composition and/or in a "Frep" composition. The antiseptic may be comprised in a pharmaceutical preparation. The pharmaceutical preparation may be formulated for topical administration. In certain embodiments, the pharmaceutical preparation is comprised on a swab. The antiseptic may comprise DMSO and DMA. The polar aprotic solvent is preferably present at a concentration that allows antiseptic active agents (alcohol and or other agents) to penetrate the membrane of a microorganism without significantly penetrating through the skin of a subject (e.g., a human subject).

In certain embodiments, the antiseptic further comprises an enhancer of alcohol penetration (e.g., a polypropylene glycol, a polyethylene glycol, a fatty acid, a soap, a non-ionic detergent, a surfactant, Triton X100, or NP40 "nonoxynol 9") or mixtures such enhancers plus aprotic solvents. In certain embodiments, the antiseptic may comprise less than about 25%, less than about 20%, less than about 15%, less than about 10%, less than about 5%, or about 4% DMSO. The antiseptic may comprise more than 50%, more than 60%, more than 65%, about 70%, more than 70%, more than 75% of the alcohol. In certain embodiments, the alcohol is isopropyl alcohol, n-propanol, ethanol, methanol, n-butanol, pentanol, hexanol, heptanol, or an isoamyl alcohol. In certain embodiments, the antiseptic further comprises an additional antimicrobial agent (e.g., an iodophor, free iodine, an antibiotic, triclosan, PCMX (chloroxylenol), chlorhexidine gluconate, a detergent, a surfactant, EDTA, EGTA, citrate, a chelator, a salt of a metal, a weak acid, or natamycin "pimaricin"). The iodine source may be iodine tincture or povidone iodine or other iodophor. The antibiotic may be colistin. The metal may be bismuth, silver, copper, or nickel. The weak acid may be acetic acid, lactic acid, or boric acid. The composition may further comprise cotton-seed oil or lanolin. In certain embodiments, the antimicrobial agent may comprise less than about 15%, less than about 10%, less than about 5%, about 1% to about 4%, about 0.1% to about 2%, or about 0.0001% to about 0.1% of the antiseptic. The antimicrobial agent may be povidone iodine or free iodine (e.g., iodine tincture). In certain embodiments, the alcohol is isopropyl alcohol; and wherein the antiseptic further comprises free iodine. In certain embodiments, the isopropyl alcohol comprises about 50% to about 80% of the antiseptic; and wherein the DMSO comprises about 1% to about 10% of the antiseptic; and wherein the free iodine comprises about 0.1% to about 5% of the antiseptic. In certain embodiments, the isopropyl alcohol comprises about 70% of the antiseptic; and wherein the DMSO comprises about 4% of the antiseptic; and wherein the free iodine comprises about 2% of the antiseptic. The antiseptic may be formulated for topical administration. In certain embodiments, the antiseptic is comprised in a swab.

Another aspect of the present invention involves a method for cleaning a surface comprising contacting the surface with an antiseptic of the present invention. The surface may be part of a medical device, such as for example, a catheter, a piece of surgical equipment, an endotracheal tube, a nephrostomy tube, a biliary stent, an orthopedic device, a prosthetic valve, a medical implant, a dental device, a dental implant, a cardiac assist device, a vascular graft, a tracheostomy, a ventriculostomy device, a intrathecal device, an indwelling catheter such as a central venous catheter, a peripheral intravenous catheter, an arterial catheter, a Swan-Ganz catheter, a hemodialysis catheter, an urinary catheter, a peritoneal catheter, an umbilical catheter, a percutaneous nontunneled silicone catheter, a cuffed tunneled central venous catheter or a subcutaneous central venbus port. The antiseptic can be included as a separate component of these device kits. In other embodiments, the surface may be a pipe or pipeline, an oil pipeline, a water pipeline, an ice machine pipe, a beverage dispensing pipe, a floor, a table-top, a counter-top, hospital equipment, or a wheel chair.

In certain embodiments, the surface is skin, preferably human skin. The method may comprise wiping the skin with a swab comprising the antiseptic solution. In certain embodiments, the surface is an oral cavity. The method may comprise contacting the oral cavity with a mouthwash or toothpaste comprising the antiseptic solution.

An aspect or the present invention relates to a swab comprising an antiseptic of the present invention. The swab may comprise a natural material (e.g., cotton) or a synthetic material. A further aspect of the present invention relates to a kit comprising the swab.

As used herein the specification, "a" or "an" may mean one or more. As used herein in the claim(s), when used in conjunction with the word "comprising", the words "a" or "an" may mean one or more than one. As used herein "another" may mean at least a second or more.

It is contemplated that any embodiment discussed in this specification can be implemented with respect to any method or composition of the invention, and vice versa. Furthermore, compositions of the invention can be used to achieve the methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

The present invention overcomes limitations in the prior art by providing an improved antiseptic. The inventor has made the surprising discovery that the inclusion of a low concentration of a polar aprotic solvent (e.g., dipolar aprotic solvents, DMSO or DMA at a concentration of less than about 30%) in an antiseptic (e.g., an antiseptic comprising an alcohol and/or an iodophor) results in a dramatic improvement in the antimicrobial properties of the antiseptic.

I. Antiseptic Compositions

Antiseptic compositions of the present invention typically comprise a polar aprotic solvent (e.g., DMSO or DMA) in combination with an alcohol. In various embodiments, antiseptic compositions of the present invention may further comprise iodine, chlorhexidine, and/or an enhancer of skin penetration. Further, it is anticipated that virtually any antiseptic compound that is presently known (e.g., Widmer and Frei, 2003) or that may be subsequently discovered may be used with the present invention. For example, octinidine, PCMX, and/or triclosan may be included in antiseptics of the present invention.

In certain embodiments where there may be a risk of fire (for example, in an environment with an oxygen mask and an electric cautery device) an antiseptic composition that has a reduced flammability may be desired. Thus, the present invention also provides antiseptic solutions comprising DMSO or DMA in combination with iodine or an iodophor, without the inclusion of an alcohol in the antiseptic solution. The below examples demonstrate that a significant portion of the efficacy of the antiseptic solution may be maintained without the inclusion of the flammable alcohol. Nonetheless, in situations where the risk of fire is reduced, antiseptic solutions comprising DMA or DMSO in combination with an alcohol and iodine may be preferred.

In embodiments involving the application of an antiseptic to the skin for the purpose of a blood draw, it is anticipated that the antiseptic compositions of the present invention will result in improvements in the quality of the blood drawn from a subject without increasing the incidence of skin irritation.

A. Polar Aprotic Solvents

Antiseptic compositions of the present invention preferably contain a polar aprotic solvent. Polar aprotic solvents (also called "dipolar aprotic solvents") are well known as "universal" solvents and include, but are not limited to, acetone, tetrahydrofuran, methyl ethyl ketone, ethyl acetate, acetonitrile, n,n-dimethylformamide (DMF), DMAC, NMP, pyridine, ether, DMSO, and DMA. In certain embodiments, antiseptic compositions of the present invention include DMSO and/or DMA. In certain embodiments, DMF, DMAC, NMP and/or acetonitrile may not be included in antiseptic compositions due to possible toxicity. In certain embodiments, acetone is included in a "Sepp" formulation at a concentration of 3 to 10%.

Dipolar aprotic solvents are aprotic and thus typically are not ionized at physiologic pH. Dipolar aprotic solvents all contain a bond that has a large bond dipole moment. This bond may be a multiple bond between carbon and either oxygen or nitrogen, such as a C-0 double bond. For example, acetone [$(CH_3)_2C=O$] and ethyl acetate ($CH_3CO_2CH_2CH_3$).

In certain embodiments, a polar aprotic solvent (e.g., DMSO) may be used to increase the antimicrobial properties of a topically applied composition. The invention is believed useful for enhancing the effectiveness of any topical water-soluble or water-based composition containing a compound or composition that is poisonous to bacteria. Thus, for example, DMSO or a similar aprotic solvent would enhance the effectiveness of triclosan, iodine, chlorine antibiotics, etc. The amount of aprotic solvent included in such compositions (e.g., less than about 30%) may preferably penetrate microbial (e.g., bacterial) membranes without substantially penetrating through the skin of the subject. In certain embodiments of the present invention, a weakly polar aprotic solvent may be included in an antiseptic instead of a strong dipolar aprotic solvent.

1. DMSO and DMA

DMSO (dimethyl sulfoxide) and DMA (N,N dimethylacetamide) are solvents that may be used to dissolve various compositions, such as pharmaceuticals. DMSO has been used at relatively high concentrations (typically 50% and higher) to deliver drugs to tissues.

Many chemists may be surprised to learn that DMSO is a natural product. In fact, DMSO occurs naturally in a variety of plants and in the oceans. DMSO, along with dimethyl sulfide and dimethylsulfone, form part of the organosulfur cycle. More than 50 billion pounds of these compounds are present naturally in the environment (i.e., in the atmosphere and in the oceans), according to calculations based on measured levels of concentrations of DMSO, DMS, and $DMSO_2$ (Dimethylsulfone).

DMSO typically produces little or no toxicity when administered to a subject. Its measured $LD_{50}$ (oral, dermal, and inhalation) show it to have a much lower acute toxicity than ethanol, acetone, and other common solvents. More importantly, DMSO is much less toxic than other dipolar aprotic solvents such as DMF, DMAC, and NMP. Recent studies show that NMP penetrates human skin at about the same rate as DMSO, and that DMF and DMAC do so at nearly the same rate. The important difference is that when DMSO enters the human body, a small amount may be converted into DMS, which can produce a garlic taste in the person's mouth. The chronic toxicity of DMSO is extremely low. In contrast, DMF and DMAC can exhibit significant chronic toxicities. Workers exposed to DMF or DMAC must be continually monitored for over-exposure. Skin and other body exposures to larger amounts of DMSO can be readily detected, because of the garlic taste produced. It is anticipated that, in certain embodiments, the amounts of DMSO contacted with a subject (e.g., a human subject) will not be sufficient to produce a garlic taste in the mouth of the subject.

It is anticipated that, in certain embodiments, DMA (N,N dimethylacetamide) may be used in combination with, or instead of DMSO in the antiseptics of the present invention to achieve improved antimicrobial properties of the antiseptic.

Antiseptic compositions of the present invention may comprise less than about 30%, more preferably less than about 25%, more preferably less than about 20%, more preferably from about 0.1% to about 25%, more preferably from about 0.1% to about 20%, more preferably from about 0.5% to about 15%, more preferably from about 0.5% to about 10%, more preferably from about 1% to about 10%, more preferably from about 2% to about 10% of DMSO or DMA. In certain embodiments, an antiseptic of the present invention may comprise about 2%, about 3%, about 4%, or about 5% of DMSO or DMA. It is anticipated that these concentrations of DMSO will result in little or no toxicity to the skin of a subject (e.g., a human).

In certain embodiments, DMSO and DMA are present in the same antiseptic. In these embodiments, the combined DMSO and DMA preferably comprises less than about 30%, more preferably less than about 25%, more preferably less than about 20%, more preferably from about 0.1% to about 25%, more preferably from about 0.1% to about 20%, more preferably from about 0.5% to about 15%, more preferably from about 0.5% to about 10%, more preferably from about 1% to about 10%, more preferably from about 2% to about 10%, or about 2%, about 3%, about 4%, or about 5% of the antiseptic.

The increase in the effectiveness of antiseptics containing a relatively low concentration of DMSO, as observed in the present invention, indicates that the DMSO may aid in disrupting the membrane structure of bacteria (e.g., grain positive and/or gram negative bacteria) and/or the DMSO may help to deliver an alcohol (which may be present in the antiseptic) to critical structures such as membrane spanning pours in the bacteria. In embodiments where an antiseptic is applied to the skin of a subject, the concentrations of DMSO of the present invention indicate that the DMSO is likely to remain primarily in the skin of the subject. For example, gram-positive cell walls are only approximately 50 nm thick. In contrast human skin is approximately 100 to 300 um thick.

B. Alcohols

The antiseptic compositions of the present invention preferably comprise an alcohol. Alcohols which may be used in antiseptic compositions of the present invention include, but are not limited to, methanol, ethanol, n-propanol, isopropanol, n-butanol, isobutanol, n-pentanol, isopentanol, hexanol, heptanol, and isoamyl alcohols. Antiseptic compositions of the present invention may include greater than 40%, more preferably greater than 45%, more preferably greater than 50%, more preferably greater than 55%, more preferably greater than 60%, more preferably greater than 65%, more preferably greater than 70% of an alcohol. In certain embodiments antiseptic compositions may contain greater than 75%, greater than 80%, or greater than 85% of an alcohol. In certain embodiments antiseptic compositions may contain less than 95% or less than 90% of an alcohol.

C. Iodine and Iodophors

Antiseptic compositions of the present invention may comprise iodine; for example, Iodine tincture (also called "tincture of iodine") or povidone iodine may be comprised in antiseptic compositions of the present invention. Povidone iodine is an iodophor (Strand et al., 1993); other presently known or subsequently discovered iodophors may be comprised in the antiseptics of the present invention.

"Free iodine", "atomic iodine", and "available iodine", as used herein, refer to the amount of $I_2$ that is present in an antiseptic composition. For example, a 10% povidone solution typically results in about 1% free iodine.

"Iodophor", as used herein, refers to a substance comprising iodine and a solubilizing agent that releases free iodine when in solution. Iodophors (e.g., povidone iodine, iodine tincture) are known in the art.

Chemical irritation of the skin may occur when contacted with 10% atomic iodine but is rare at 2% formulations. It is anticipated that the atomic iodine in the antiseptics of the present invention will result in little or no toxicity to the subject. When applied to the skin of a subject, iodine, like alcohol, typically rapidly binds and denatures proteins in the stratum corneum. In certain embodiments, povidone iodine may be preferred to iodine tincture, as povidone iodine may result in reduced contamination and less skin irritation as compared to iodine tincture (Little et al., 1999). In other embodiments, however, 2% iodine tincture may be more effective in killing a bacteria (e.g., a *Staphylococci*) without producing a greater rate of skin irritation as compared to povidone iodine.

Antiseptics of the present invention may preferably comprise less than 10%, more preferably less than about 9%, more preferably less than about 8%, more preferably less than about 7%, more preferably less than about 6%, more preferably less than about 5%, or about 4%, about 3%, about 2%, or about 1% of atomic iodine (e.g., as released from an iodophor such as iodine tincture or povidone iodine).

D. Enhancers of Skin Penetration

Antiseptics of the present invention may comprise an enhancer of alcohol penetration. "Enhancer of alcohol penetration", as used herein, refers to a compound which aids the absorption of an alcohol into the skin of a subject. Enhancers of alcohol penetration include various polypropylene glycols (PG), polyethylene glycols (PEG), fatty acids, soaps, non-ionic detergents, and surfactants (e.g., nonionic surfactants). Triton X100 is an example of a detergent. NP40 ("nonoxynol 9") is an example of a nonionic surfactant.

E. Antimicrobial Agents

The compounds of the present invention may comprise an antimicrobial agent. "Antimicrobial", as used herein refers to the ability of a compound to selectively kill a bacteria, a fungi, a protozoan, an algae, or a virus. For example, certain *cryptococcus* oils possess antifungal activity and may be included in compositions of the present invention. Triclosan is an example of an antimicrobial agent that has antibacterial properties and may be included in compositions of the present invention.

1. Chlorhexidine

Chlorhexidine, also referred to as chlorhexidine gluconate, is an antimicrobial agent that may also be comprised in the antiseptic compositions of the present invention. Chlorhexidine may be used to reduce contamination of blood samples (Barenfanger et al., 2004).

Antiseptics of the present invention preferably comprise less than 10%, more preferably less than about 9%, more preferably less than about 8%, more preferably less than about 7%, more preferably less than about 6%, more preferably less than about 5%, or about 4%, about 3%, about 2%, or about 1% of chlorhexidine.

II. Pharmaceutical Preparations and Application of Antiseptics

The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one antiseptic (containing DMSO or DMA, and an alcohol) or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 1990, incorporated herein by reference). Except insofar as any conventional carrier is incompatible with the active ingredient, its use in the pharmaceutical compositions is contemplated.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additional prevention of the action of microorganisms can be brought about by including preservatives such as various antibacterial and antifungal agents, including but not limited to parabens (e.g., methylparabens, propylparabens), chlorobutanol, phenol, sorbic acid, thimerosal or combinations thereof.

The actual dosage amount of a composition of the present invention administered to a subject (e.g., a human patient) may be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

A. Topical Pharmaceutical Preparations

Pharmaceutical compositions for topical administration may be in the form of an antiseptic solution or in another form such as an ointment, a paste, or a cream. Ointments include all oleaginous, adsorption, emulsion and water-solubly based compositions for topical application, while creams and lotions are those compositions that include an emulsion base only. Topically administered medications may, in certain embodiments, include glycerin, an alkyl methyl sulfoxide, a pyrrolidone and/or luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture.

Various formulations for topical application of an antiseptic of the present invention are contemplated. For example, an antiseptic may be topically applied in a skin sanitizing solution (e.g., a skin sanitizer that does not require washing with water, a solution containing soap that is preferably washed away using water), in a swab, and/or in a kit containing multiple swabs which may be used to clean the skin of a subject.

B. Application of an Antiseptic Using a Swab

In certain embodiments, an antiseptic of the present invention may be applied (e.g., topically) using a swab. Swabs are well known in the art and include alcohol swabs. Swabs may be used for disinfection of the skin of a subject (Goldman et al., 1997).

Swabs may be made of any suitable material including natural (e.g., cotton) and synthetic (e.g., DACRON, Nylon, rayon) materials. Typically, the swab is constructed of a material that can adsorb a solution (e.g., an alcohol solution).

Swabs may be used to apply a solution to and/or disinfect the skin of a subject. In certain embodiments, a swab is used to clean the skin of a subject prior to drawing blood from the subject in order to reduce the chances of contamination of the blood. In other embodiments, a swab may be used to apply an antiseptic solution and/or clean the skin of a subject prior to, during, or after a surgical procedure. It is recognized that both human and non-human subjects may benefit from the present invention. Additionally a swab may be used to apply an antibacterial solution to and/or clean surgical tools, medical equipment, and/or any other object where it is desired to reduce contamination by microorganisms.

C. Contact Time Using an Antiseptic

Antiseptics of the present invention may be contacted with a surface (e.g., the skin of a subject, surgical equipment) for a period of time of several seconds to several minutes or more. The antiseptic may be contacted with a surface on only one occasion in a procedure, or the antiseptic may be contacted with the surface more than once or repeatedly. When the antiseptic is repeatedly contacted with a surface, the antiseptic may be in the same preparation or in different preparations.

For example, to perform a "high level antiseptics", a two stage process is typical. The first step involves a low level disinfectant/cleaning step, and this step is referred to as a "Frep". During the Frep, a composition (e.g., containing a soap, an alcohol and/or acetone) may be used to de-fat and clean the skin of a subject, e.g., removing dirt, protein, fats, and loosely held colonizing bacteria.

The second step involves application of a higher concentration of disinfectant that is allowed an extended contact time (e.g., several minutes) in order to achieve maximum antisepsis, and this step is referred so as a "Sepp". The Sepp is applied after the Frep. In certain embodiments of the present invention, the Sepp may be performed using a solution containing about 50% to about 70% of isopropyl alcohol or ethanol, about 2% iodine, and about 3-5% DMSO.

In other embodiments, a single application of an antiseptic may be used. For example, a single alcohol pad may be used to clean the skin of a subject in certain circumstances where low level antisepsis is acceptable, such as routine phlebotomy for clinical chemistry tests.

III. Cleaning Surfaces with Antiseptics

The compositions of the present invention can be used to reduce microbial agents from the surface of a medical device such as a catheter, an endotracheal tube, a nephrostomy tube, a biliary stent, an orthopedic device, a prosthetic valve, a medical implant, dental devices or dental implants, cardiac assist devices, vascular grafts, tracheostomy, ventriclulostomy devices, or intrathecal devices. In some aspects, the catheter is an indwelling catheter such as a central venous catheter, a peripheral intravenous catheter, an arterial catheter, a Swan-Ganz catheter, a hemodialysis catheter, an urinary catheter, a peritoneal catheter, an umbilical catheter, a percutaneous nontunneled silicone catheter, a cuffed tunneled central venous catheter or a subcutaneous central venous port.

In other embodiments, the methods of the invention are useful in reducing microbial agents from a surface such as an organic surface or an inorganic surface. An organic surface is exemplified by skin, surgical sutures, mucosal membrane surface, or an epithelial surface. An inorganic surface may be the surface of a pipe or pipeline, a floor, a table-top, a countertop, hospital equipment, or a wheel chair, etc. Non-limiting examples of a pipe is an oil pipeline, a water pipeline, an ice machine pipe, or a beverage dispensing pipe.

It is contemplated that the antimicrobial or antiseptic solutions of the present invention will find particular usefulness as antimicrobial mouthwash solutions. Such mouthwash solutions are contemplated to be useful both in conjunction with dental procedures and oral sterilization as well as in general dental and oral hygiene applications. Antimicrobial mouthwash is becoming extremely important in the prevention of oral cavity infections as well as aspiration pneumonia. Microbial organisms in the mouth particularly around the teeth, embed themselves in biofilm and the pathogenesis of infection and colonization is similar to that seen in, for example, vascular catheters. In this regard, it is contemplated that one will preferably apply a solution containing an alcohol (preferably ethanol) and a dipolar aprotic solvent (preferably DMSO) as a mouthwash or mouth flush solution. In certain embodiments, a second mouthwash can be used that contains a pleasant flavor (e.g., mint, menthol, etc) in order to reduce any possible lingering unpleasant tastes from the dipolar aprotic solvent (e.g., DMSO). Concentrations of an alcohol (preferably ethanol) for the mouthwash contemplated include from about 1% to about 35%, more preferably from about 5% to about 30%, and in certain embodiments from about 15% to about 27%. The dipolar aprotic solvent (e.g., DMSO) may be in the mouthwash at the same concentrations contemplated for antiseptic compositions or in lower concentrations. A second antimicrobial compound (e.g., triclosan) may also be present in the mouthwash. In certain embodiments, the toothpaste may contain about 0.5-5% DMSO, about 10% ethanol, and triclosan.

In other embodiments, antiseptics of the present invention may be used in toothpaste in order to improve the antimicrobial properties of the toothpaste. The toothpaste would include a dipolar aprotic solvent (e.g., DMSO) at the same or a similar concentrations as contemplated for antiseptic or mouthwash compositions of the present invention. The toothpaste may or may not contain an alcohol (preferably ethanol). If present, the alcohol may be present at a concentration of from about 5% to about 15%, although concentrations of up to about 35% may be used in toothpastes of the present invention. A second antimicrobial compound (e.g., triclosan) may also be present in the toothpaste.

Microorganisms that attach themselves to inert surfaces, such as medical devices including, vascular catheters, endotracheal tubes, Foley catheters, biliary stents, nephrostomy tubes, prosthetic valves, ventriculostomy or epidural catheters, or fluid pipelines, such as oil pipelines or water pipelines, produce a layer made of exopolysaccharide called microbial biofilm. These organisms embed themselves in this layer. This biofilm layer ultimately becomes the protective environment that shields these organisms on the inert surface from the antimicrobial activity of various antibiotics or antiseptics. In U.S. Pat. Nos. 5,362,754 and 5,688,516, incorporated herein by reference in their entirety, the present inventor demonstrated that a combination of one or more antimicrobial agent with one or more chelator and/or anticoagulant (such as EDTA or heparin) reduces or eradicates these antibiotic-resistant biofilm embedded microorganisms if the antimicrobial and chelator combination is allowed to dwell on the surface for at least 4 hours. However, in both clinical and environmental situations, it is typically not feasible to allow a 4 hour dwell time for the chelator and antimicrobial agent to reduce or eradicate the microbes. For example, it is not possible to interrupt the therapy of critically ill patients receiving continuous infusion therapy through a vascular catheter for 4 hours. It is also not possible to interrupt an environmental situation involving fluid pipelines for 4 hours to allow for such a prolonged dwell time of antimicrobial/chelator solution. In certain embodiments, an antiseptic solution of the present invention can be applied to an inert surface or a medical device for a period of less than 4 hours and achieve substantial killing of microorganisms.

IV. Antimicrobial Properties of Antiseptics

An antiseptic of the present invention may be used to destroy the microbes that cause an infectious diseases (e.g. a viral, bacterial, protozoan, or fungal disease). The infectious disease may affect a human or non-human animal. In certain embodiments, an antiseptic of the present invention may be contacted with the skin of a subject (e.g., a human patient) to destroy a fungi, a bacteria, a virus, and/or a protozoan.

"Antimicrobial", as used herein (e.g., "antimicrobial agents" or "antimicrobial compositions"), refers to the ability of a compound to destroy a microorganism (e.g., skin flora, a bacterium, or a fungus) or a virus. It is also appreciated that, in certain embodiments of the present invention, certain antimicrobial compositions of the present invention can also result in cleaning other compounds (e.g., chemical and/or biological toxins) from the skin of a subject when administered applied topically (e.g., when a swab containing the antimicrobial composition is wiped against the skin of the subject). Antimicrobial compositions of the present invention, in certain embodiments, are formulated for topical administration. It is appreciated that virtually all presently known, or subsequently discovered, antimicrobial compositions may be used with the present invention. Antimicrobial compositions of the present invention preferably result in little or no toxicity to the subject. Antimicrobial compositions include alcohols, iodine, chlorhexidine, surfactants (e.g., soaps), detergents, other solvents (e.g., acetone), and the like.

A. Fungal Diseases

An antiseptic may be used to destroy, inactivate, dissolve, and/or remove a fungi; for example, in certain embodiments of the present invention, an antiseptic may be applied to the skin of a subject to destroy a fungi that is present on the skin of the subject. The fungi may cause a fungal disease in a subject (e.g., a human). The fungi may be presently known or subsequently discovered. It is anticipated that virtually any kind of fungi may be affected by antiseptic compositions of the present invention. Fungi and fungal diseases are well known in the art. Fungal and other mycotic pathogens (some of which are described in Beneke (1979); Smith (1989); and Scrip's Antifungal Report (1992). Dermatophytosis and Dermatomycosis (Rippon, 1988); Rippon et al., (1993) are responsible for a variety of diseases in humans, ranging from mycoses involving skin, hair, or mucous membranes, such as, but not limited to, Aspergillosis, Black piedra, Candidiasis, Chromomycosis, Cryptococcosis, Onychomycosis, or Otitis externa (otomycosis), Phaeohyphomycosis, Phycomycosis, Pityriasis versicolor, ringworm, Tinea barbae, Tinea capitis, Tinea corporis, Tinea cruris, Tinea favosa, Tinea imbricata, Tinea manuum, Tinea nigra (palmalis), Tinea pedis, Tinea unguium, Torulopsosis, Trichomycosis axillaris, White piedra, and their synonyms, to severe systemic or opportunistic infections, such as, but not limited to, Actinomycosis, Aspergillosis, Candidiasis, Cliromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and Torulopsosis, and their synonyms, some of which may be fatal. Known fungal and mycotic pathogens include, but are not limited to, *Absidia* spp., *Actinomadura madurae, Actinomyces* spp., *Allescheria boydii, Alternaria* spp., *Anthopsis deltoidea, Apophysomyces elegans, Arnium leoporinum, Aspergillus* spp., *Aureobasidiun pullulans, Basidiobolus ranarum, Bipolaris* spp., *Blastomyces dermatitidis, Candida* spp., *Cephalosporium* spp., *Chaetoconidium* spp., *Chaetomium* spp., *Cladosporium* spp., *Coccidioides immitis, Conidiobolus* spp., *Corynebacterium tenuis, Cryptococcus* spp., *Cunninghamella bertholletiae, Curvularia* spp., *Dactylaria* spp., *Epidermophyton* spp., *Epidermophyton floccosum, Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur, Microsporum* spp., *Mucor* spp., *Mycocentrospora acerina, Nocardia* spp., *Paracoccidioides brasiliensis, Penicillium* spp., *Phaeosclera dematioides, Phaeoannellomyces* spp., *Phialemonium obovatum, Phialophora* spp., *Phoma* spp., *Piedraia hortai, Pneumocystis carinii, Pythium insidiosum, Rhinocladiella aquaspersa, Rhizomucor pusillus, Rhizopus* spp., *Saksenaea vasiformis, Sarcinomyces phaeomuriformis, Sporothrix schenckii, Syncephalastirum racemosuin, Taeniolella boppii, Torulopsosis* spp., *Trichophyton* spp., *Trichosporon* spp., *Ulocladium chartarum, Wangiella dermatitidis, Xylohypha* spp., *Zygomyetes* spp. and their synonyms. Other fungi that have pathogenic potential include, but are not limited to, *Thermomucor indicae-seudaticae, Radiomyces* spp., and other species of known pathogenic genera. These fungal organisms are ubiquitous in air, soil, food, decaying food, etc. *Histoplasmoses, Blastomyces,* and *Coccidioides*, for example, cause lower respiratory infections. *Trichophyton rubrum* causes difficult to eradicate nail infections. In some of the patients suffering with these diseases, the infection can become systemic causing fungal septicemia, or brain/meningal infection, leading to seizures and even death.

Fungal organisms which attack immunocompromised patients are often called "opportunistic fungi." These may be opportunistic yeast's or other molds, such as described above.

Aspergillosis is the most common mold infection in patients with hematological cancer, with *Aspergillus fumigatus* being the offending cause in more than 90% of the infected patients. Aspergillosis is a term that encompasses a variety of disease processes caused by *Aspergillus* species. *Aspergillus* species are ubiquitous; their spores are constantly being inhaled. Of the more than 300 species known, only some are ordinarily pathogenic for man and these include: *A. fumigatus, A. flavus, A. niger, A. nidulans, A. terreus, A. sydowi, A. flavatus*, and *A. glaucus*. Aspergillosis is increasing in prevalence and is particularly a problem among patients with chronic respiratory disease or immunocompromised patients. Among immunocompromised patients, aspergillosis is second only to candidiasis as the most common opportunistic mycosis and accounts for about 15% of the systemic mycoses in this group. Opportunistic pulmonary aspergillosis is characterized by widespread bronchial erosion and ulceration, followed by invasion of the pulmonary vessels, with thrombosis, embolization and infarction. Clinically, infection manifests as a necrotizing patchy bronchopneumonia, sometimes with hemorrhagic pulmonary infarction. In about 40% of eases, there is hematogenous spread to other sites. Aspergillosis is also a rare but devastating complication of traumatic wounds, such as, burn wounds, frost bite wounds, or wounds developed by diabetics, where amputation is often required for cure. Invasive aspergillosis is commonly fatal, so aggressive diagnosis and treatment is required. Detection of *Aspergillus* infection is difficult as blood, urine and cerebrospinal fluid cultures are rarely positive, however, the fungi can be seen in smears and biopsies from infected tissue.

B. Viral Diseases

An antiseptic may be used to destroy, inactivate, dissolve, and/or remove a virus; for example, in certain embodiments of the present invention, an antiseptic may be applied to the skin of a subject to destroy a virus that is present on the skin of the subject. The virus may cause a viral disease in a subject (e.g., a human). The virus may be presently known or subsequently discovered. Viruses and viral diseases are well known in the art. Viral diseases include, but are not limited to: influenza A, B and C, parainfluenza (including types 1, 2, 3, and 4), paramyxoviruses, Newcastle disease virus, measles, mumps, adenoviruses, adenoassociated viruses, parvoviruses, Epstein-Barr virus, rhinoviruses, coxsackieviruses, echoviruses, reoviruses, rhabdoviruses, lymphocytic choriomeningitis, coronavirus, polioviruses, herpes simplex, human immunodeficiency viruses, cytomegaloviruses, papillomaviruses, virus B, varicella-zoster, poxviruses, rubella, rabies, picornaviruses, rotavirus, Kaposi associated herpes virus, herpes viruses type 1 and 2, hepatitis (including types A, B, and C), and respiratory syncytial virus (including types A and B).

C. Bacterial Diseases

Certain antiseptic compositions of the present invention have antibacterial properties. These antiseptic compositions may be used to kill and/or remove bacteria from an object or subject. It is anticipated that antiseptics of the present invention may be used to affect (e.g., damage and/or kill) virtually any kind of bacteria that is known or may be discovered.

An antiseptic may be used to destroy, inactivate, dissolve, and/or remove a bacteria; for example, in certain embodiments of the present invention, an antiseptic may be applied to the skin of a subject to destroy a bacteria that is present on the skin of the subject. The bacteria may cause a bacterial disease in a subject (e.g., a human). The bacteria may be presently known or subsequently discovered.

In certain embodiments, antiseptic compositions of the present invention may be contacted with bacteria that may exist on the skin of a subject. Bacteria including *Staphylococcus* spps such as *S. epidermidis*, Gram negative rods such as *Acinetobacter* spps, yeasts such as *T. glabrata, Streptococcus* spps and *Propionibacterium* spps. such as *P. acnes* can extensively colonize sweat glands, hair follicles, and sebaceous glands; thus, in certain embodiments, the antiseptics of the present invention may be used to destroy any and/or all of these bacteria. Furthermore, skin bacteria can be trapped in enclosed pockets formed by layering of cornified skin cells, which is referred to as "lacunar sequestration" of bacteria. In certain embodiments of the present invention, an antiseptic can be used to destroy both bacteria on the surface of skin as well as lacunar bacteria.

Bacteria and bacterial diseases are well known in the art. Bacterial diseases include, but are not limited to, infection by the 83 or more distinct serotypes of pneumococci, streptococci such as *S. pyogenes, S. agalactiae, S. equi, S. cants, S. bovis, S. equinus, S. anginosus, S. sanguis, S. salivarius, S. mitis, S. mutans*, other viridans streptococci, peptostreptococci, other related species of streptococci, enterococci such as *Enterococcus faecalis, Enterococcus faecium*, Staphylococci, such as *Staphylococcus epidermidis, Staphylococcus aureus*, particularly in the nasopharynx, *Hemophilus influenzae, pseudomonas* species such as *Pseudomonas aeruginosa, Pseudomonas pseudomallei, Pseudomonas mallei*, brucellas such as *Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticium, Corynebacterium urealyticum, Corynebacterium hemolyticum, Corynebacterium equi*, etc. *Listeria monocytogenes, Nocordia asteroides, Bacteroides* species, Actinomycetes species, *Treponema pallidum, Leptospirosa* species and related organisms. The invention may also be useful against gram negative bacteria such as *Klebsiella pneumoniae, Escherichia coli, Proteus, Serratia* species, *Acinetobacter, Yersinia pestis, Francisella tularensis, Enteiobacter* species, *Bacteriodes* and *Legionella* species and the like.

D. Protozoan Diseases

An antiseptic may be used to destroy, inactivate, dissolve, and/or remove a protozoan; for example, in certain embodiments of the present invention, an antiseptic may be applied to the skin of a subject to destroy a protozoan that is present on the skin of the subject. The protozoan may cause a protozoan disease in a subject (e.g., a human). The protozoan may be presently known or subsequently discovered. Protozoa and protozoan diseases are well known in the art. Protozoan or macroscopic diseases include infection by organisms such as *Cryptosporidium, Isospora belli, Toxoplasma gondii, Trichomonas vaginalis, Cyclospora* species, for example, and for *Chlamydia trachomatis* and other *Chlamydia* infections such as *Chlamydia psittaci*, or *Chlamydia pneumoniae*, for example.

V. Packaging and Kits

Antiseptics of the present invention may be included in a kit. For example, an antiseptic solution may be provided in a kit to be administered as a catheter flush solutions. In other embodiments, an antiseptic in a swab (e.g., as a Sepp or Frep). The kit will optionally include an instruction sheet insert to identify how the kit is to be used.

The kits of the present invention contain an antiseptic of the present invention (e.g., present in a swab, present alone in a container means, etc). Additional components may also be present in the kit and/or in the antiseptic solution, such as for example, an antibiotic (e.g., minocycline), a chelator/anticoagulant (e.g., EDTA), or other antimicrobial agent. The kit may comprise of one or two or three or more compartments.

The components of the kit may be provided in separate compartments or in the same compartment. The components of the kit may be provided separately or mixed. The mixed components may contain two or more agents such as an antibiotic, a chelator/anticoagulant or additional component.

In certain embodiments, an antiseptic solution of the present invention may be combined with an additional powdered or non-liquid antimicrobial compound. In these embodiments, a Wet/Wet® dual chamber container system or a Liquid/Dry® dual container system, available from Becton-Dickinson, may be used in various embodiments of the present invention where it is desirable to mix one or more component (e.g., antibiotic, chelator/anticoagulant, etc) with an antiseptic solution or the present invention, typically just prior to use.

The container means of the kits will generally include at least one vial, test tube, flask, bottle, syringe or other container means, into which the antiseptic solution may be placed, and preferably, suitably aliquoted. Where an additional antibiotic or antimicrobial agent or additional component is provided, the kit may also contain a second, third or other additional container into which this component may be placed. The kits of the present invention may also include a means for containing the antiseptic solution, antimicrobial agent, chelator/anticoagulant, and/or any other reagent containers in close confinement for commercial sale. Such containers may include injection or blow-molded plastic, or glass containers into which the desired vials are retained.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Development of Improved Skin Antiseptics

This example presents data concerning antiseptic compositions. The addition of 2-8% DMSO to an antiseptic composition resulted in an approximately a 1 to 3 log increase in bacterial killing in vitro. Skin antiseptics are used prior to routine phlebotomy, in preparation for surgery and as part of routine infection control hand-washing practices. These antiseptics could have a substantial impact on post surgical wound infections, nosocomial infections, and on diagnostic tests such as blood culture (contamination), or on blood product quality (platelet contamination). According to the NISS (CDC's National Nosocomial Infection Surveillance System) studies conducted by the CDC (U.S. Centers for Disease Control), nosocomial infections cost over 7 billion dollars annually in the US. Additional avoidable costs are associated with contamination of diagnostic tests. There are 25M blood cultures performed each year in the US, with a contamination rate of 4-6%. (2.5B costs). The antiseptics presented in this Example may be used to decrease contamination rates.

Procedure for In Vitro Antiseptic Evaluation.

In the studies represented below the procedure can be used to produce mature, thick-walled, sessile, bacterial cells. These cells are then exposed simultaneously to 50% isopropanol/water agent and to 50% isopropanol with the addition of 4% DMSO. The bacteria are transferred simultaneously using a multichannel pipette, thus there are no differences in time of exposure to the bactericidal agents. The procedure was performed as follows:

1. Inoculate bacteria in 20 ml TSB broth media for overnight growth.
2. Collect bacterial cells at 3000 g, 20 min.
3. Re-suspend in buffered isotonic saline.
4. Age at room temp 24-72 hr.
5. Collect at 3000 g, 20 min.
6. Re-suspend in minimal volume of sterile water or normal saline; mix well.
7. Expose to antiseptic (with or without DMSO) 20-30 sec. (Use a 12 channel multichannel pipette to transfer cells to 6 wells of test and 6 wells of control antiseptic simultaneously)
8. Rapidly dilute in TSB broth.
9. Plate matched dilutions on SBA agar, spread for colony counting.
10. Incubate 24 hr, 35° C. and count.

Results for Antiseptic Testing

The effectiveness of various concentrations of DMSO in a 70% isopropyl alcohol on bacterial killing is shown below in Table 1.

TABLE 1

Coagulase Negative *Staphylococcus* (CNS) in 70% isopropanol +/− DMSO.

| % DMSO | # of Plates | mean number colonies/plate | SD |
|---|---|---|---|
| 22.5 | 6 | 0 | 0 |
| 11.2 | 6 | 0 | 0 |
| 5.6 | 12 | 63.2 | 10 |
| 2.8 | 6 | 145.8 | 7.8 |
| 0 | 12 | 293.7 | 74.4 |

Antiseptic exposure for 30 sec.
Plates were counted at 24 hr.

In vitro results of skin antiseptics comprising isopropanol, iodine, and DMSO are shown against *S. epidermidis* (ATCC 12228) in Table 2. These results indicate that inclusion of 4% DMSO resulted in a clear and dramatic reduction in colony formation.

TABLE 2

Addition of DMSO increases Potency of Topical Antiseptic Solutions vs CNS

| Experiment | Dilution | IPI | DIPI |
|---|---|---|---|
|  |  | Colony counts at 24 hr |  |
| Oct. 6, 2004 | 1/64 | 313 | 1 |
|  | 1/64 | 399 | 5 |
|  | 1/256 | 146 | 1 |
| Oct. 10, 2004 | 1/27 | 116 | 0 |
|  | 1/81 | 51 | 0 |

IPI—Isopropanol(70%) + Iodine(2%)
DIPI—DMSO(4%) + Isopropanol(70%) + Iodine(2%)

Coagulase negative *Staphylococcus* (CNS) as (*S. epidermidis* ATCC12228) added to 70% IP, 2% Iodine vs. 70% IP, 2% Iodine, 4% DMSO. Inocula, dilutions, alcohol concentrations, and exposure times are all exactly paired. CNS (*S. epidermidis*) are the most frequent skin flora contaminants.

In Vitro Effect of IPI vs DIPI on CNS was evaluated. Coagulase negative *Staphylococcus* (CNS)—ATCC12228 was added to a solution of 70% isopropyl alcohol, 2% Iodine (IPI) or a solution of 70% isopropyl alcohol, 2% Iodine, 4% DMSO (DIPI). Inocula, dilutions, alcohol concentrations, and exposure times are all exactly paired. Agar plates cultured with either of these solutions indicate that more bacteria were killed by the solution containing DMSO. The plates containing DMSO showed reduced numbers of surviving bacteria.

*E. coli*, a typical gram negative rod bacteria, responds in a manner similar to CNS. In Vitro Effects of IP vs DIP on *E. coli* were evaluated. *E. coli* were added to a solution of 70% isopropyl alcohol (IP) or a solution of 70% isopropyl alcohol, 4% DMSO (DIP). Inocula, dilutions, alcohol concentrations, and exposure times are all exactly paired. Agar plates cultured with either of these solutions indicate that more bacteria were killed by the solution containing DMSO. Again, a clear and dramatic reduction in colony formation is observed as a result of the presence of DMSO.

Similar enhancement of kill is seen for *Pseudomonas aeruginosa*, a gram negative rod frequently associated with nosocomial infections. In Vitro effects of isopropyl alcohol with or without DMSO on *P. aeruginosa*. *P. aeruginosa* were added to a solution of 70% isopropyl alcohol (IP) or a solution of 70% isopropyl alcohol, 4% DMSO (DIP). Inocula, dilutions, alcohol concentrations, and exposure times are all exactly paired. Agar plates cultured with either of these solutions indicate that more bacteria were killed by the solution containing DMSO. The results demonstrate bacteria killing as a result of the presence of DMSO in the sanitizing solution.

Table 3 shows antiseptic enhancement by the inclusion of 4% DMSO for a variety of microbes. In Table 3, "IP" indicates a 70% isopropyl alcohol solution, and "DIP" indicates a 70% isopropyl alcohol+5% DMSO solution.

TABLE 3

Additional in vitro antiseptic results

| Date | Microbe | IP | DIP |
|---|---|---|---|
| Oct. 8, 2002 | CNS Pt. | 250 | 30 |
| Oct. 17, 2002 | CNS Pt | 15 | 0 |
| Oct. 21, 2002 | CNS Pt | 200 | 0 |
| Oct. 27, 2002 | CNS Pt | 147 | 10 |
| Apr. 21, 2002 | A. baumani | ~1500 | 8 |
| Apr. 28, 2002 | A. baumani | 47 | 2 |
| Jun. 16, 2002 | A. baumani | TNC | 188 |
| | | TNC | 168 |
| May 2001 | P. aeruginosa | 190 | 38 |
| | | 380 | 71 |
| Jun. 5, 2001 | P. aeruginosa | 188 | 0 |
| | | 248 | 2 |
| Jun. 15, 2001 | E. coli | 192 | 0 |
| | | 128 | 0 |
| Jun. 16, 2001 | E. coli | 53 | 6 |
| | | 43 | 3 |
| Jun. 30, 2001 | E. coli | 1248 | 0 |
| | | 1174 | 0 |

TABLE 4

Various isopropanol concentrations vs. 5% W or 5% DMSO.

| % alcohol | Colony number | Ratio (W/D). |
|---|---|---|
| 60 D (DMSO 5%) | 5 | |
| 60 W* (water control) | 1546 | (319) |
| 50 D | 21 | |
| 50 W | 912 | (43) |
| 40 D | 2268 | |
| 40 W | 2500 | (~1) |
| 30 D | ~10,000 | |
| 30 W | ~10,000 | (~1) |
| 20 D | ~50,000 | |
| 20 W | ~50,000 | (~1) |
| 10 D | TNC | |
| 0 D | TNC | |

Conclusion: High alcohol concentrations are required for both maximum bactericidal effect and maximum synergy with DMSO.

Table 4 shows the effect of various concentrations of isopropanol with 5% DMSO ("D") or without DMSO ("W") on coagulase negative *staphylococcus*. (For example, "50 D" indicates a solution with 50% isopropyl alcohol and 5% DMSO; "50 W" indicates a solution with 50% isopropyl alcohol without DMSO.) Coagulase negative *staphylococcus* ATCC 29212 were grown 24 hr Bactec 26+, saline at 35° C. 24 hr. Aged cells were then exposed to antiseptics and rapidly diluted in Trypticase soy broth, and equal (50 ul) amounts were plated for counting. (CNS counts are shown at each condition after 24 hr growth 35° C.). CNS counts at various dilutions and with various isopropyl concentrations. Additional data from further experiments is shown below.

DETAIL OF EXPERIMENT 112204 "Effect of various concentrations of isopropanol on coagulase negative *staphylococcus*".

| isopropyl | "1:3" | "1:9" | "1:27" |
|---|---|---|---|
| 60% + 5% W | 1596 | 380 | 1572 |
| 60% + 5% DMSO | 5 | 1 | 4 |
| 50 + 5W | 912 | 189 | 196 |
| 50 + 5D | 21 | 15 | 17 |
| 40 + 5W | 2268 | 1500 | 3000 |
| 40 + 5D | 2500 | 1500 | 1000 |
| 30 + 5W | ~10,000 | 10,000 | 5000 |
| 30 + 5D | ~10,000 | 10,000 | 5000 |
| 20 + 5W | ~50,000 | 50,000 | 10,000 |
| 20 + 5D | ~50,000 | 50,000 | 10,000 |
| 10 + D | ~150,000 | 50,000 | 50,000 |
| 0 + D | ~300,000 | 150,000 | 50,000 | coagulase negative *staphylococcus* ATCC 29212 were grown 24 hr Bactec 26+, saline and incubated at 35o c. 24 hr.
Aged cells were then exposed to antiseptics and rapidly diluted in Trypticase soy broth, and equal (50 ul) amounts were plated for counting, (cns counts are shown at each condition after 24 hr growth 35o C.)
Conclusion: In this experiment the DMSO enhancement effect decreases rapidly at alcohol concentrations of 30% and below.

The killing effect of DMSO in combination with various concentrations of isopropyl alcohol on Coagulase Negative *Staphylococcus* (CNS) *Staphylococcus epidermidis* (CNS) ATCC 29212 bacteria is shown above. These results indicate that the effect of DMSO (5%) was observed to be effective when in combination with 40% or more of isopropanol. The killing effect of DMSO was even more pronounced when added to solutions containing 50% isopropanol, and even more pronounced when used in combination with 60% isopropanol.

TABLE 5

CNS (ATCC12228) Colony Formation in the Presence of Sanitizers

| 50% Etoh + 1% I | 50% Etoh + 4% DMSO + 1% I |
|---|---|
| 2360 | 76 |
| 1730 | 58 |
| 400 | 5 |
| 384 | 3 |

Table 5 demonstrates that improvements in antibacterial effects can be achieved by the inclusion of DMSO in a sanitizer. The inventor has found that Ethanol and isopropanol work equally well. The property of small amounts of DMSO enhancing killing of high percentage alcohol solutions applies to various alcohols.

DMSO was shown to enhances killing of CNS. Coagulase negative *Staphylococcus* (CNS)—ATCC12228 were added to solutions containing 50% ethanol+1% Chlorhexidine, or a solution containing 50% ethanol+4% DMSO+1% Chlorhexidine. CNS was prepared as stated above but with the use of chlorhexidine containing antiseptics. Inocula, dilutions, alcohol concentrations, and exposure times are all exactly paired. Agar plates cultured with either of these solutions indicate that more bacteria were killed by the solution containing DMSO. Again, the presence of DMSO reduced colony formation.

This enhanced performance indicates that the invention is not limited to alcohol based antiseptics by is also effective with aqueous based antiseptics. The invention is believed useful for enhancing the effectiveness of any aqueous system containing a compound or composition that is poisonous to bacteria. Thus, DMSO or a similar aprotic solvent would enhance the effectiveness of triclosan, iodine, chlorhexidine, PCMX, octinidal, chlorine antibiotics, etc. The amount of aprotic solvent will preferably penetrate bacterial membranes but not substantially penetrate the skin of the subject.

The toxicity of REMOSO is well studied—REMOSO (50% DMSO) is associated with little toxicity when applied to intact skin. In-vitro studies using the antiseptics of this example show a 1 to 3 log increase in killing when compared to the current standard formula for *Staphylococcus epidermidis*, *P. aeruginosa*, and *E. coli*. The antiseptics may be compared in outpatients who have been scheduled to receive blood culture as part of their care. Standard or Test skin antiseptic can be used in a random manner and the rate of skin flora contamination can be tracked. Since iodine is the agent associated with all of the toxicities (skin irritation, or allergic reactions) and that the iodine concentration is the same between both groups that no impact on patient toxicity is anticipated.

The inventor has incorporated 2-8% DMSO into isopropanol based antiseptic formulations and found approximately 1 to 2 log enhanced killing of a variety of bacteria in vitro. Antiseptics are used prior to major and minor surgery, for hand hygiene, and in routine phlebotomy. Current topical antiseptics have a failure rate of 4-6%. A 2-8% content of DMSO dramatically increases the killing rate of conventional alcohol based skin antiseptics.

Bacterial decontamination of normal skin is difficult to achieve. As shown herein, the inventors have found that DMSO (2-8%) improved bactericidal activity of 70% isopropanol or iopropanol/iodine by approximately 10 fold or more. The DMSO probably assists alcohol penetration to the bacterial cell wall (~0.1 µm) where pores and other critical structures are denatured. Human skin contains a dead keratinized layer (100 µm) containing no critical structures. The DMSO solution should be innocuous to normal skin.

It is unlikely that significant toxicity will result from inclusion of DMSO in an antiseptic. DMSO 10% is used routinely in freezing media for bacteria and mammalian cells. Thus, the mechanism of action in our novel antiseptic is unlikely to relate to direct toxicity. The improved killing effect is probably related to enhanced penetration of bacterial cell walls by DMSO allowing enhanced penetration of the bactericidal agent—i.e. a small % of DMSO facilitates penetration of alcohol, chlorhexidine, or iodine. Most bacteria have membrane pores and other critical structures within the 0.1 µm thick bacterial cell wall. Thus, a small enhancement in penetration of the bactericidal agent can have a pronounced effect on survival. In contrast, human skin has a thick (100-300 µm) layer of dead keratinized cells in the stratum corneum, which contains no critical structures. A 4% DMSO/alcohol tincture is not sufficient to have carrier effects in human skin. (Wilson et al., 1965).

Example 2

Skin Antiseptics Containing DMSO Reduce Contamination In Vivo

Skin antiseptics containing DMSO were tested on 52 patients over a 3 year period. A dramatic improvement in the reduction in contamination was observed (Table 6).

TABLE 6

In vivo results - Approved protocol:

| | (52 patients over a 3 year period) | |
|---|---|---|
| Clinical Results- LAB01-321: | IPI | DIPI |
| Contamination | 5 | 0 |
| # Tested | 30 | 22 |

IPI—Isopropanol(70%) + Iodine(2%)
DIPI—DMSO(4%) + Isopropanol(70%) + Iodine(2%)

Additional large-scale clinical trials are possible. Typically, during clinical testing, early stopping rules would apply if toxicity is observed. A change from 0.1 to 1% in skin irritation would be detected in the first 1000 patients in each arm with a power of 77%. A change from 2.5% to 0.5% for Coagulase Neg Staphylococci will have 93% power after the first 1000 patients in each arm.

Example 3

DMA Functions Similar to DMSO Skin Antiseptics

In this example, a dramatic improvement in the antimicrobial attributes of an antiseptic was achieved by including N,N-Dimethylacetimide (DMA) in the antiseptic composition. The inclusion or absence of 5% N,N-Dimethylacetimide (DMA) in antiseptic compositions containing varying concentrations of isopropanol were tested for antimicrobial properties. The test organism used for antiseptic evaluation was *S. epidermidis* (12228). The antiseptic was contacted with the *S. epidermidis* for approximately 30 sec. All other conditions were similar to conditions described in Example 1. The results of these experiments are summarized in Table 7 below.

Well, the initial contact between the antiseptic and the bacterial cells is arbitarily called 1x. Solutions were then diluted rapidly to stop the killing. 1/3 is the first dilution well 1/9 is the second dilution and so forth. These dilution wells are rapidly plated (still as temporally linked pairs—using a multichannel pipettor) and this effects a further dilution of the antiseptic.

TABLE 7

Colony count number of CNS on BAP at 24 hr 35o C.

| Isopropanol %, | DMA % | Plate dilutions | | |
|---|---|---|---|---|
| | | 1:3 | 1:9 | 1:27 |
| 60 | 5 | 0-0 | 0 | 0 |
| 60 | 0 (5% water) | 1-0 | 0 | 0 |
| 50 | 5 | 0-0 | 1 | 0 |
| 50 | 0 | 4-1 | 1 | 1 |
| 40 | 5 | 31-12 | 3 | 2 |
| 40 | 0 | 139-76 | 13 | 4 |
| 30 | 5 | 1580-2740 | 2000 | 423 |
| 30 | 0 | 40,000-50,000 | 10,000 | 2,200 |
| 20 | 5 | $10^6$-$10^6$ | $10^6$ | $10^5$ |
| 20 | 0 | $10^6$-$10^6$ | $10^6$ | $10^5$ |
| 10 | 5 | >$10^6$->$10^6$ | $10^6$ | $10^6$ |
| 10 | 0 | >$10^6$->$10^6$ | $10^6$ | $10^6$ |

These above studies demonstrate that DMA shows an enhancing effect of the antimicrobial properties of an antiseptic composition similar to DMSO.

Additional studies involving testing a series of isopropanol dilutions mixed with and without 5% DMA were performed using various dilutions.

As shown in Table 8, an enhancement of the antimicrobial properties of the antiseptic composition were produced by the inclusion of DMA. The test organism is again ATCC 12228 *Staphylococcus epidermidis* (also referred to herein as CNS—coagulase negative *staphylococcus*), which is the most common normal flora of human skin.

The timing of these studies is critical, and simultaneous transfer into the dilutants is achieved by using a multi-channel pipettor. In these studies, higher concentrations of alcohol resulted in a high degree of microbial killing; however, an enhancement by DMA can still be observed at lower concentrations (Table 8).

TABLE 8

Colony counts of CNS

| Isopropanol % | DMA % | dilution 1:6 | 1:36 | 1:216 |
|---|---|---|---|---|
| 60 | 5 | 0 | 0 | 0 |
| 60 | 0(5% water) | 0 | 0 | 0 |
| 50 | 5 | 0 | 0 | 0 |
| 50 | 0 | 2 | 0 | 0 |
| 40 | 5 | 25 | 7 | 0 |
| 40 | 0 | 84 | 23 | 3 |
| 30 | 5 | 1720 | 638 | 59 |
| 30 | 0 | >3000 | 1120 | 260 |
| 20 | 5 | 50,000* | 50,000* | 50,000* |
| 20 | 0 | 50,000 | 50,000 | 50,000 |
| 10 | 5 | 1 × 10E6* | 500,000* | 500,000* |
| 0 | 0 | 1 × 10E6 | 500,000 | 500,000 |

The * indicates that the pair of plates with and without DMA were very similar visually and the number is based on the closest match to one of the standard photographs.

Example 4

Skin Antiseptics Containing DMSO and Iodine

Additional aqueous formulations in the absence of alcohol can also be made that incorporate the novel properties conferred by the addition of a polar aprotic solvent.

There is a need for improved antiseptics in the operating room that are completely non-flammable. The incorporation of 18% DMSO into aqueous povidone iodine demonstrates a useful example of such an antiseptic composition. The skilled artisan will realize that various concentrations may be effective.

DMSO containing povidone iodine formulations (D %) vs. Water (W %) when added to a standard 10% povidone iodine solution.

TABLE 9

DMSO or Water added to 10% povidone iodine

| Antiseptic | Dilutions | | |
|---|---|---|---|
| | 1/4 | 1/16 | 1/27 |
| W18% | 273 | 41 | 14 |
| D18% | 2 | 14 | 3 |
| W6 | 0 | 93 | 22 |
| D6 | 0 | 26 | 12 |
| W2 | 2 | 91 | 24 |
| D2 | 2 | 56 | 21 |

(W6 = water 6%; W2 = water 2%; "D6" = DMSO 6%; "D2" = DMSO 2%)

In Table 9, Antiseptics were mixed with a dense suspension of *S. epidermidis* (ATCC 12228) and incubated for 30 sec. The samples were then diluted 1/4, 1/16, 1/27 into Tryptic soy broth and immediately plated as pairs using a multichannel pipette. These pairs were immediately spread for colony counting on Sheep Blood Agar plates. Results show average colony counts of duplicate samples Sheep Blood agar plates at 48 hr.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,671,654
Barenfanger et al., *J. Clin, Microbiol.,* 42(5):2216-2217, 2004.
Bates, *JAMA,* 265:365-369, 1991.
Beneke, In: *Human Mycoses*, Upjohn Co., MI, 1979.
Boyce, *Emerging Infectious Dis* 7:231, 2001
Goldman et al., *Transfusion,* 37(3):309-312, 1997.
Little et al., *Am. J. Med.,* 107(2):119-125, 1999.
Remington's Pharmaceutical Sciences, 18th Ed. Mack Printing Company, 1990.
Rippon and Fromtling, In: *Cutaneous antifungal agents, selected compounds in clinical practice and development*, Marcel Dekker, NY, 1993.

Rippon, In: Medical Mycology, 3rd Ed., W B Saunders, Philadelphia, Chapt. 8, 1988.
Scrip's Antifungal Report, PJB Publications Ltd, 1992
Smith, In: Opportunistic mycoses of man and other animals, CAB Intl., Wallingford, UK, 1989.
Strand et al., JAMA, 269(8):1004-1006, 1993.
Trautner et al., Infect. Control Hospt. Epidemology, 23(7), 2002.
Widmer and Frei, In: Manual of Clinical Microbiology, Murray (Ed.), Amer. Soc. Microbiology Press, 2003.
Wilson et al. Toxicol Appl Pharmacol., 7:688, 1965.

The invention claimed is:

1. An antiseptic comprising (a) DMSO or DMA, (b) ethanol or isopropyl alcohol and (c) free iodine or chlorhexidine, wherein the ethanol or isopropyl alcohol comprises about 50% to about 80% of the antiseptic; the DMSO or DMA comprises from 1% to 8% of the antiseptic; and the free iodine or chlorhexidine comprises about 0.1% to about 5% of the antiseptic, wherein the antiseptic is formulated for topical administration onto a surface.

2. The antiseptic of claim 1, further defined as comprising DMSO, ethanol or isopropyl alcohol and free iodine or chlorhexidine.

3. The antiseptic of claim 2, comprising from 2% to 8% DMSO and from 1% to 5% free iodine.

4. The antiseptic of claim 1, further defined as comprising DMA, ethanol or isopropyl alcohol and free iodine or chlorhexidine.

5. The antiseptic of claim 4, comprising from 2% to 8% DMA and from 1% to 5% free iodine.

6. The antiseptic of claim 1, wherein the antiseptic is comprised in a Sepp composition.

7. The antiseptic of claim 1, wherein the antiseptic is comprised in a Frep composition.

8. The antiseptic of claim 1, wherein the antiseptic is comprised in a pharmaceutical preparation.

9. The antiseptic of claim 8, wherein the pharmaceutical preparation is formulated for topical administration.

10. The antiseptic of claim 9, wherein the pharmaceutical preparation is comprised on a swab.

11. The antiseptic of claim 1, wherein the antiseptic further comprises an enhancer of alcohol penetration.

12. The antiseptic of claim 11, wherein the enhancer of alcohol penetration is a polypropylene glycol, a polyethylene glycol, a fatty acid, a soap, a non-ionic detergent, a surfactant, Triton X100, or NP40 ("nonoxynol 9").

13. The antiseptic of claim 1, wherein the antiseptic further comprises an additional antimicrobial agent.

14. The antiseptic of claim 13, wherein the antimicrobial agent is an iodophor, free iodine, an antibiotic, triclosan, PCMX (chloroxylenol), chlorhexidine gluconate, a detergent, a surfactant, EDTA, EGTA, citrate, a chelator, a salt of a metal, a weak acid, or natamycin (pimaricin).

15. The antiseptic of claim 13, wherein the antimicrobial agent comprises less than about 15% of the antiseptic.

16. A method for cleaning a surface comprising contacting the surface with an antiseptic of any one of claim 6-10, 11, 12, 13, 14, 15, 1 or 2-5.

17. The method of claim 16, wherein the surface is part of a medical device.

18. The method of claim 16, wherein the surface is a pipe or pipeline, an oil pipeline, a water pipeline, an ice machine pipe, a beverage dispensing pipe, a floor, a table-top, a counter-top, hospital equipment, or a wheel chair.

19. The method of claim 16, wherein the surface is skin.

20. The method of claim 16, wherein the surface is an oral cavity.

21. The method of claim 20, wherein the method comprises contacting the oral cavity with a mouthwash or toothpaste comprising the antiseptic solution.

22. A swab comprising an antiseptic of any one of claim 6-10, 11, 12, 13, 14, 15, 1 or 2-5.

* * * * *